(12) United States Patent
Osgood et al.

(10) Patent No.: US 9,177,770 B2
(45) Date of Patent: Nov. 3, 2015

(54) ION GATE METHOD AND APPARATUS

(75) Inventors: Mark A. Osgood, Brookline, NH (US); Ching Wu, Acton, MA (US)

(73) Assignee: Excellims Corporation, Acton, MA (US)

( * ) Notice: Subject to any disclaimer, the term of this patent is extended or adjusted under 35 U.S.C. 154(b) by 663 days.

(21) Appl. No.: 12/763,092

(22) Filed: Apr. 19, 2010

(65) Prior Publication Data

US 2010/0200745 A1 Aug. 12, 2010

Related U.S. Application Data

(63) Continuation-in-part of application No. 11/776,392, filed on Jul. 11, 2007, now abandoned, and a continuation-in-part of application No. 11/946,679, filed on Nov. 28, 2007, now Pat. No. 7,943,901.

(60) Provisional application No. 61/170,628, filed on Apr. 19, 2009.

(51) Int. Cl.
    *H01J 49/06* (2006.01)
    *G01N 27/62* (2006.01)
    *C07B 63/00* (2006.01)

(52) U.S. Cl.
    CPC ............ *H01J 49/061* (2013.01); *G01N 27/622* (2013.01); *C07B 63/00* (2013.01); *Y10T 29/49227* (2013.01)

(58) Field of Classification Search
    CPC ............ H01J 49/061; H01J 1/88; G21K 1/04
    USPC ............... 250/324, 396 R, 287, 288
    See application file for complete search history.

(56) References Cited

U.S. PATENT DOCUMENTS

| 3,999,263 | A  | * | 12/1976 | Marshall et al. | ................ 445/36 |
| 4,150,319 | A  |   | 4/1979  | Nowak           |                         |
| 5,028,983 | A  | * | 7/1991  | Bickford et al. | ............. 257/668   |
| 5,465,480 | A  |   | 11/1995 | Karl            |                         |
| 5,599,730 | A  | * | 2/1997  | Lee et al.      | ....................... 438/448 |
| 6,664,545 | B2 | * | 12/2003 | Kimmel et al.   | ........... 250/396 R   |
| 7,120,998 | B2 |   | 10/2006 | LeCursi         |                         |
| 7,569,835 | B2 | * | 8/2009  | Frederick et al.| ......... 250/396 R     |
| 7,579,589 | B2 | * | 8/2009  | Miller et al.   | .................. 250/292 |
| 7,763,853 | B2 | * | 7/2010  | Walsh           | ............. 250/326   |
| 2003/0146392 | A1 |  | 8/2003  | Kimmel         |                         |
| 2004/0231150 | A1 | * | 11/2004 | Charles et al. | .................. 29/825 |
| 2005/0173629 | A1 | * | 8/2005  | Miller et al.  | .................. 250/290 |
| 2005/0189488 | A1 | * | 9/2005  | Pai et al.     | ...................... 250/292 |
| 2005/0258514 | A1 | * | 11/2005 | Smith et al.   | .................. 257/619 |
| 2006/0192105 | A1 |  | 8/2006  | Zare           |                         |
| 2007/0063138 | A1 |  | 3/2007  | Ruiz-Alonso    |                         |
| 2007/0176270 | A1 |  | 8/2007  | Zuleta         |                         |
| 2007/0272875 | A1 |  | 11/2007 | Frederick      |                         |
| 2008/0021343 | A1 | * | 1/2008  | Hashimshony et al. | ...... 600/547      |
| 2008/0230688 | A1 | * | 9/2008  | Bowdler et al. | ............... 250/282 |

* cited by examiner

*Primary Examiner* — Brooke Purinton

(57) ABSTRACT

The present invention generally relates to systems and methods for transmitting beams of charged particles, and in particular to such systems and methods that employ defecting at least one set of grid elements into the same plane to form an ion gate. In addition, an operation method of closing a gate involving alternating voltages on the adjacent gate wires is described.

6 Claims, 8 Drawing Sheets

ION GATE METHOD AND APPARATUS

CROSS-REFERENCE TO RELATED APPLICATIONS

The present application is a continuation in part of U.S. patent application Ser. No. 11/776,392, filed on Jul. 11, 2007, and is a continuation in part of U.S. patent application Ser. No. 11/946,679, filed on Nov. 28, 2007, and claims the benefit of and priority to corresponding U.S. Provisional Patent Application No. 61/170,628, filed Apr. 19, 2009 respectively, the entire content of these cross-referenced applications is herein incorporated by reference.

BACKGROUND OF THE INVENTION

Many analytical instruments, such as ion mobility spectrometers (IMS), can require a gating device for turning on and off a flowing stream of ions and/or other charged particles. IMS are widely used in field chemical analysis. IMS separate ionic species based on their ion mobility in a given media (either gas or liquid). Recent development of the IMS technology results in two forms of IMS instruments and systems. The time-of-flight (TOF) IMS separate ions based on their steady state ion mobilities under constant electric field. High resolving power with IMS has been achieved with the TOF-IMS instruments. Alternatively, devices that separate ions based their mobility changes under high field conditions, such as field asymmetric ion mobility spectrometer (FAIMS) or differential mobility spectrometer (DMS), can also be used.

Even though the gating device is a minor component in the overall design of an IMS, if manufactured correctly, this component can improve the IMS resolution and system performance. The gating device is used to regulate the injection of ion packets into the analytical instrument. There are many deficiencies with the current approaches for manufacturing gating devices.

SUMMARY OF THE INVENTION

The present invention generally relates to systems and methods for transmitting beams of charged particles, and in particular to such systems and methods that employ defecting at least one set of grid elements into the same plane, such that the grid elements are interleaved.

In one embodiment of the present invention, at least one electrically substrate (conducting or non-conducting) is used to deflect at least one set of the grid elements into the same plane, such that the grid elements are interleaved. The ion gate has a first and second set of electrically isolated grid elements that lie in the same plane where the respective sets of grid elements are applied to alternate potentials. The advanced grid manufacturing methods and features are disclosed.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

DETAILED DESCRIPTION OF VARIOUS EMBODIMENTS

Figure 1:
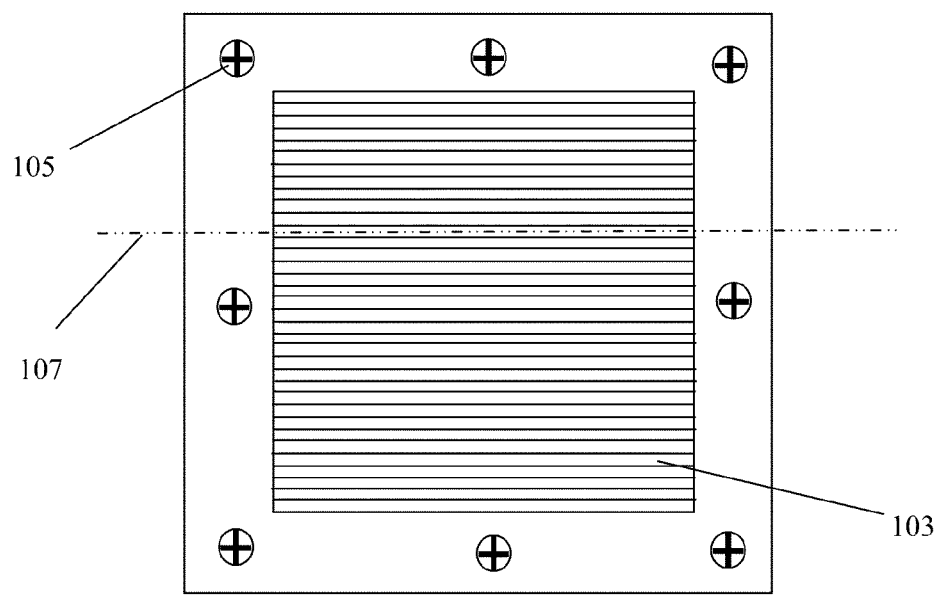
FIG. 1 shows the completed ion gate from a front view.

The term ion mobility separator, and ion mobility spectrometer, and ion mobility based spectrometers are used interchangeably in this invention, often referred to as IMS, including time-of-flight (TOF) IMS, differential mobility spectrometers (DMS), field asymmetric ion mobility spectrometers (FAIMS) and their derived forms. A time of flight ion mobility spectrometer and their derived forms refers to, in its broadest sense, any ion mobility based separation device that characterize ions based on their time of flight over a defined distance. A FAIMS, a DMS, and their derived forms separate ions based on their ion mobility characteristics under high values of normalized electric field.

The systems and methods of the present inventions may make use of "drift tubes." The term "drift tube" is used herein in accordance with the accepted meaning of that term in the field of ion mobility spectrometry. A drift tube is a structure containing a neutral gas through which ions are moved under the influence of an electrical field. It is to be understood that a "drift tube" does not need to be in the form of a tube or cylinder. As understood in the art, a "drift tube" is not limited to the circular or elliptical cross-sections found in a cylinder, but can have any cross-sectional shape including, but not limited to, square, rectangular, circular, elliptical, semi-circular, triangular, etc. In many cases, a drift tube is also referred to the ion transportation and/or ion filter section of a FAIMS or DMS device.

Neutral gas is often referred to as a carrier gas, drift gas, buffer gas, etc. and these terms are considered interchangeable herein. The gas is at a pressure such that the mean free path of the ion, or ions, of interest is less than the dimensions of the drift tube. That is the gas pressure is chosen for viscous flow. Under conditions of viscous flow of a gas in a channel, conditions are such that the mean free path is very small compared with the transverse dimensions of the channel. At these pressures the flow characteristics are determined mainly by collisions between the gas molecules, i.e. the viscosity of the gas. The flow may be laminar or turbulent. It is preferred that the pressure in the drift tube is high enough that ions will travel a negligible distance, relative to the longitudinal length of the drift tube, therefore a steady-state ion mobility is achieved.

The phrase "and/or," as used herein in the specification and in the claims, should be understood to mean "either or both" of the elements so conjoined, i.e., elements that are conjunctively present in some cases and disjunctively present in other cases.

Unless otherwise specified in this document the term "particle" is intended to mean chemical and/or biological single or plurality of sub-atomic particle, atom, molecule, large or macro molecule, nanoparticle, or other matters that are vapor, droplets, aerosol, liquid, solid that follow a mobile medium, where the medium can be a gas, a liquid, supercritical fluid and/or other fluidic materials.

The present invention generally relates to systems and methods for transmitting beams of charged particles, and in particular to such systems and methods that employ defecting at least one set of grid elements into the same plane.

As used herein, the term "grid element" generally refers to wire, rod, cable, thin metal foil piece that can be planar, square, rectangular, circular, elliptical, semi-circular, triangular, but not limited to these examples. The grid element can be made of any electrically conducting material.

The term "gate element" generally refers to a structure that includes one or more grid elements that can be spatially arranged with a gap between each other.

Figure 6:
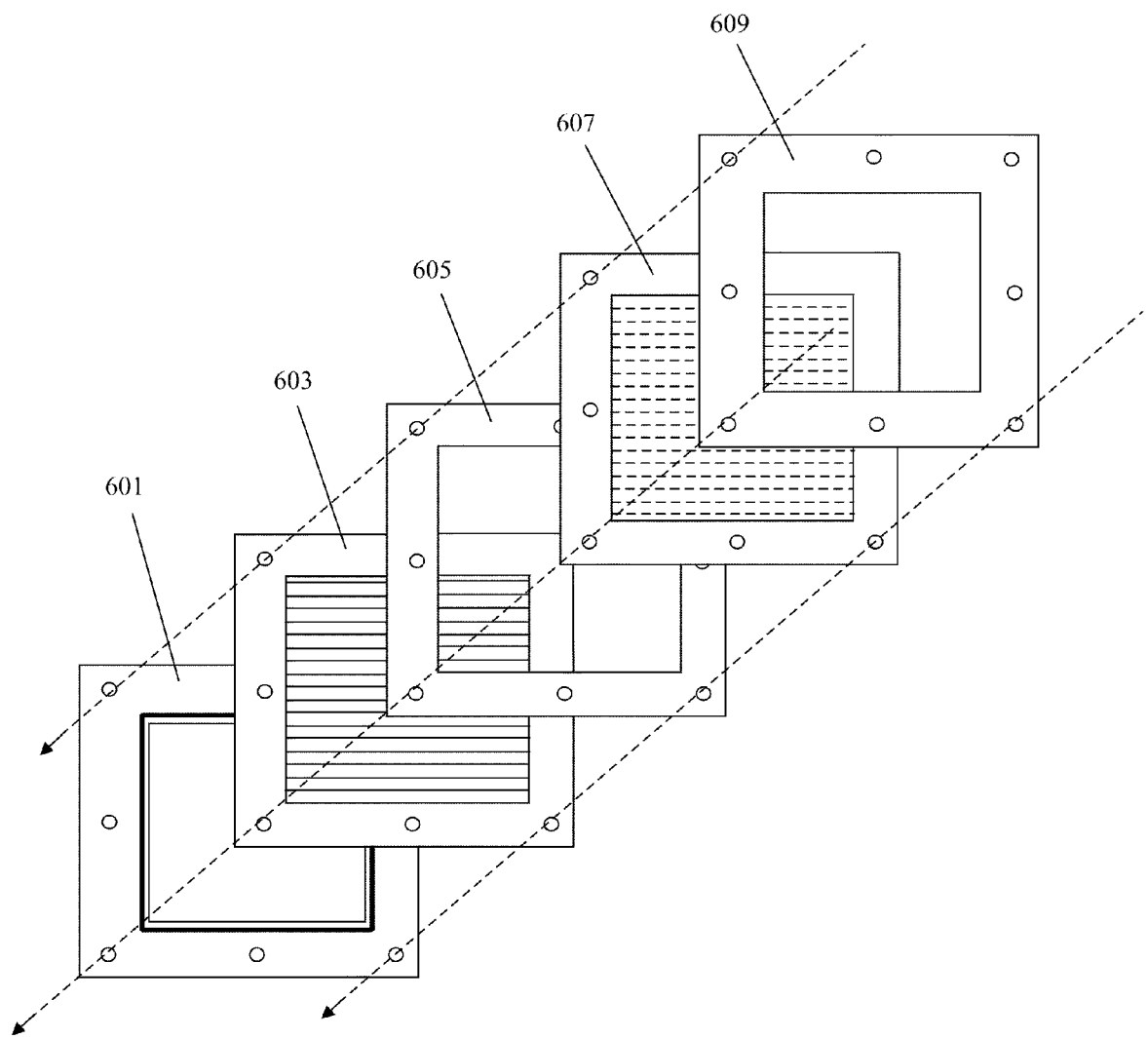
FIG. 6 illustrates the process of manufacturing the ion gate.

One aspect of the invention relates to manufacturing an ion gate in such a way that the ion gate can be produced in a simple, reproducible, and reliable manner. FIG. 6 illustrates a non-limiting process for manufacturing the ion gate. This method for manufacturing an ion gate for a charged particle stream begins with the fabrication of the gate elements 603 and 607 that includes the grid elements. Each of the gate elements 603 and 607 are made so that the two different pairs of grid elements can be interleaved without contacting each other. Followed by assembling an insulating layer (electrically non-conductive, the insulating layer can be any size and shape, such as a square or a disk with openings, or a washer, that allows a different potential to the gate elements) 605 between the gate elements 603 and 607 to electrically isolate the gate elements. The substrate throughout this patent is typically non-conducting, but can also be a conducting material for some applications. Then two electrically non-conductive substrates 601 and 609 are added to deflect the grid elements in the gate elements into the same plane. FIG. 6 shows a non-limiting example, wherein two electrically non-conductive substrates are used. Similarly, one electrically non-conductive substrate can also be used to manufacture the ion gate. Finally, the gate elements are secured together along with the electrically non-conductive substrates and the insulating layer. In an alternative embodiment, the gate elements can be segmented, thus each segment of the grid elements can be operated independently, i.e. open and close at different timing, as a segmented ion gate. The method for manufacturing an ion gate for a charged particle stream, can comprise of electrically isolated grid elements that lie in the same plane. The respective sets of grid elements can be applied to alternate potentials to close the gate and the same potential to open the gate. For example, the grid element is at 100 volts above and 100 volts below the reference potential. The reference potential is the potential at the particular location of the gate in the drift tube. The steps used to manufacture the ion gate can be in any order and comprise: fabricating at least two gate elements, wherein each gate element includes at least one set of grid elements; assembling an insulating layer between the gate elements; deflecting at least one set of grid elements into the same plane of the other set of grid elements with at least one substrate; and securing the gate elements and the non-conductive substrates together.

A non-limiting example of the completed ion gate is shown in FIG. 1. The shape of the ion gate can be: square (shown), oval, circle, semicircle, triangle, rectangle, polygon, octagon, but not limited to these examples. FIG. 1 shows a front view of the completed ion gate. The ion gate includes gate elements that contain the grid elements 103 are held in place with several screws 105. The ion gate apparatus that is used for gating a charged particle stream comprises: at least two sets of grid elements that individual voltages can be applied to each set to open and close; and at least one substrate for deflecting at least one set of grid elements into the same plane of the other sets of grid elements. In addition an electrically insulating layer can be added to allow different voltages to be set to each set of grid elements.

Another aspect of the invention relates to providing an ion gate with an effective gating function by applying a uniform tension on the grid elements, fabricating the gate elements such that the grid elements are equally spaced, and deflecting the grid elements into the same plane.

Figure 2:
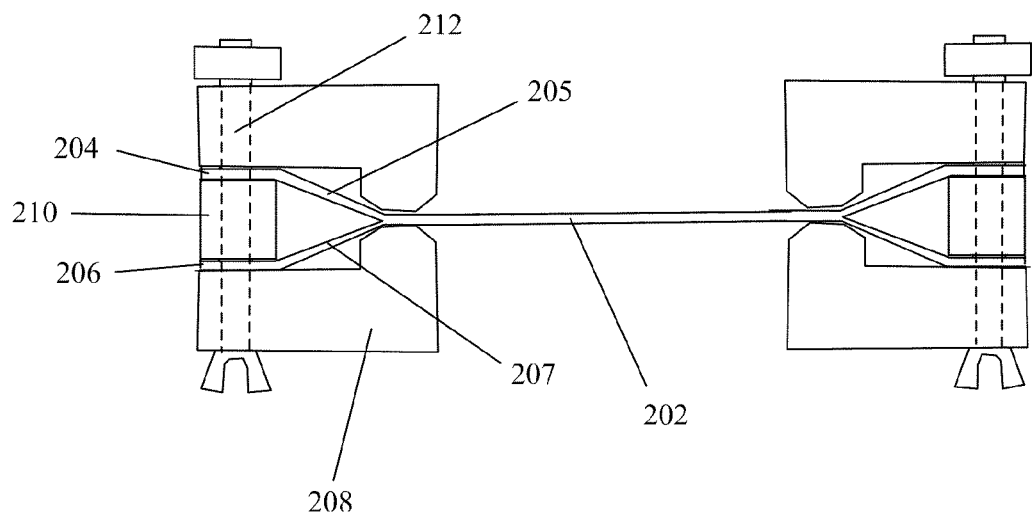
FIG. 2 shows a cross-sectional top view of the ion gate.
Figure 5A:
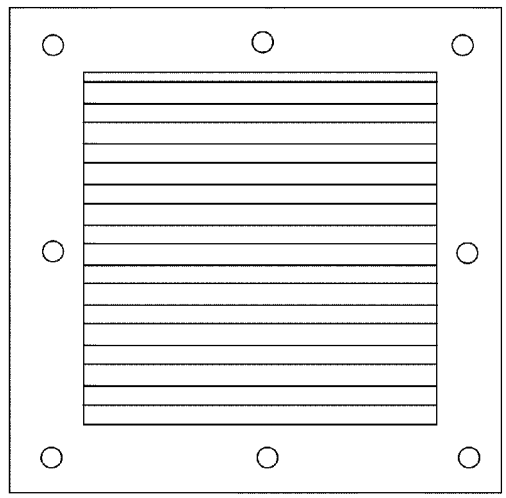
FIGS. 5A-5C illustrates the respective sets of gate elements.
Figure 5B:
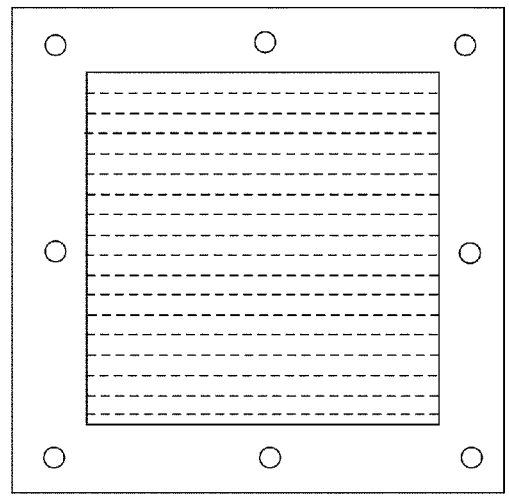
Figure 5C:
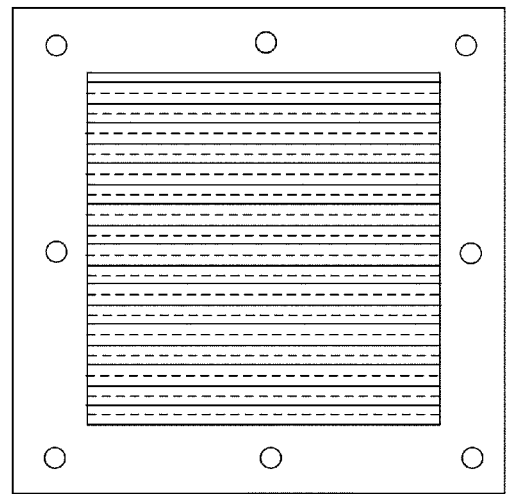

FIG. 2 shows a cross-sectional top view of the ion gate. The cross-section shown in FIG. 2 is indicated in FIG. 1 with a cutting line 107. The ion gate comprises a first and second electrically isolated gate elements 204 and 206 that each have at least one grid element 205 and 207. The electrically non-conductive or conductive substrate 208 deflects the grid element 207 which is part of the gate element 206 into the same plane as the deflected grid element 205 which is part of the gate element 204. The gate elements 204 and 206 are electrically isolated by placing an insulating layer (electrically non-conductive or conductive) 210 between these gate elements. The grid elements are deflected into the same plane 202 and are electrically isolated by interleaving these sets of grid elements with a gap between each grid element. FIG. 5C illustrates the respective sets of grid elements in FIG. 5A and FIG. 5B interleaved. In FIG. 2, the ion gate components are secured together with a screw fastener 212. In this non-limiting example, ether an electrically non-conducive material screw fastener may be used or a conductive material fastener can be contained in an electrically non-conductive standoff (not shown).

Figure 3A:
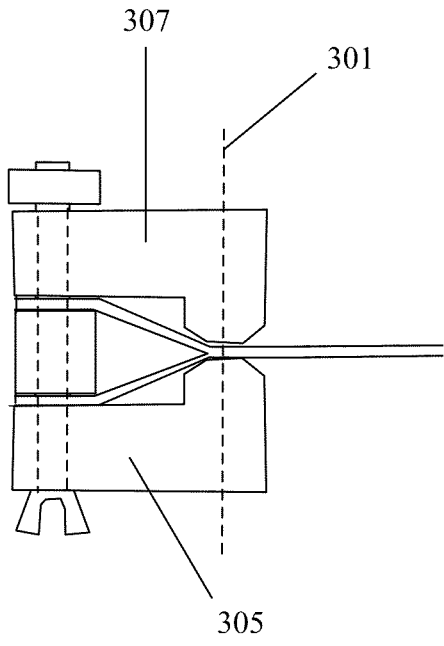
FIGS. 3A and 3B show two different methods to deflect the grid elements.
Figure 3B:
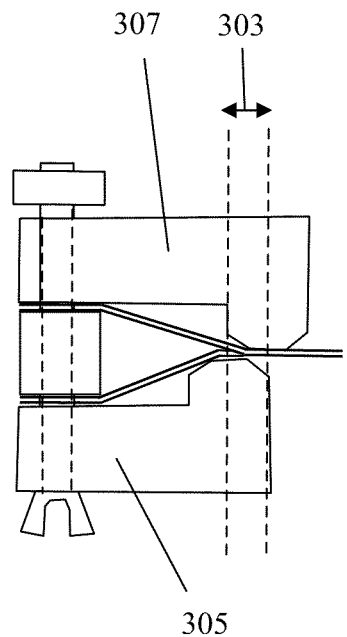

One embodiment of the present invention, involves using off-set electrically non-conductive or conductive substrates to deflect the grid elements. FIG. 3A shows the electrically substrates 305 and 307 with no off-set 301. FIG. 3B shows electrically substrates 305 and 307 with an off-set 303. This off-set design may allow uniform deflection of grid elements and low cost manufacturing.

Figure 4:
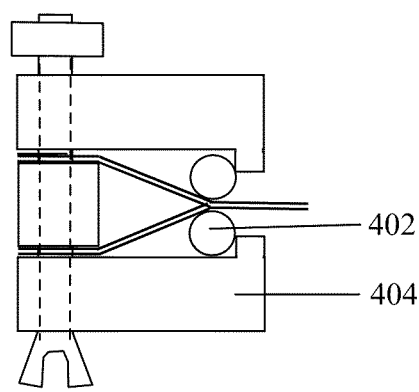
FIG. 4 shows an alternative method to deflect the grid elements.

Another embodiment of the present invention, involves the shape of the electrically non-conductive or conductive substrate to deflect the grid elements. The portion that deflects the grid element can be in the shape of a wedge, hexagon, semi-circle, but not limited to these examples. In addition, the electrically non-conductive substrate portion that deflects the grid element can be independent to the secured electrically non-conductive substrate. A non-limiting example is shown in FIG. 4, where a circular (not limited to only this shape) substrate 402 deflects the grid element and the secured substrate 404 holds the substrate 402 in place.

Yet another embodiment of the present invention is the fabrication of the gate elements. The grid elements within the gate elements can be produced by cutting, etching, evaporation or electroplating, but not limited to these methods. In a non-limiting example, parallel rows of grid elements are formed by removing portions of a given thickness of planar metal foil by etching portions from the foil. This method forms a plurality of grid elements that are equally spaced. In addition to forming equally spaced grid elements within the gate element, the grid elements are made from the same gate element material as a single entity. In this manner, the grid elements do not need to be fixed to the gate element through gluing (epoxy), glass soldering, or any other attaching manner. Fabricating the gate elements by etching the grid elements is a robust and reproducible method for manufacturing the grid elements. In addition, since no gluing, soldering, or other attaching manner is used in fabricating the gate elements, elevated temperatures and/or thermal expansion of the grid elements are all uniform. The photo chemical milling (etching) can be performed on one side or both sides of the material being etched.

Figure 7A:
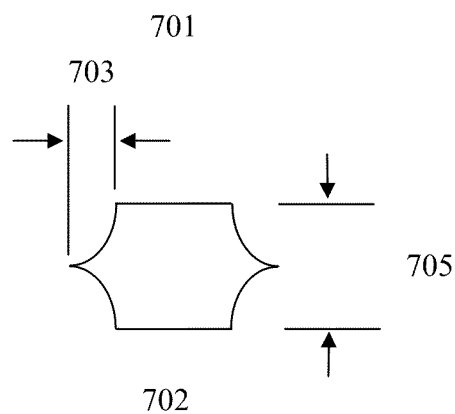
FIG. 7A-7C shows the photo etched edges of the grid elements.
Figure 7B:
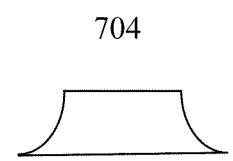
Figure 7C:
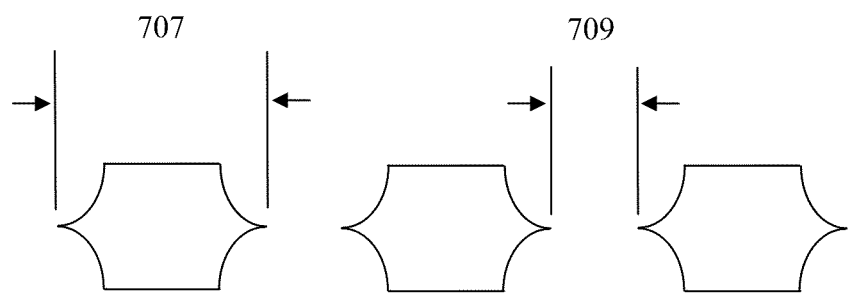

FIG. 7A shows the shape (a pair of opposing concave fillets) of the grid element etched on both sides of the material, etched from the top 701 and the bottom 702 of the material. FIG. 7B shows the shape (a concave fillet) of the grid element etched on one side of the material, etched from only the top side 704 of the material. The etched edge distance 703 may be smaller or greater than the material thickness 705 depending on the layout of the grid elements. For example, the etched edge distance to the material thickness ratio is greater than zero, in particular 1-50%, 50-100%, 100-500%. FIG. 7C shows three grid elements that are etched on both sides of the material. Photo chemical milling can produce uniform dimensions in grid element width 707 and gap 709 between grid elements forming a plurality of grid elements that are equally spaced. When the ion gate is a uniform product, injection of ion packets into the drift tube are tight packets with limited background signal, therefore a higher signal to noise ratio can be achieved. In this embodiment, regardless of manufacturing methods, the grid element is to be made with a sharp edge, the geometry may generate a narrow gating electric field region resulting in high precision gating of charge particles. In an IMS device, a narrow ion pulse could be generated with precision gate timing control. An ion gate apparatus for gating a charged particle stream comprises: at least two sets of electrically insulated grid elements on the same plane, the evenly spaced grid elements have at least one sharp edge face to adjacent grid element.

Another embodiment of the present invention is securing the gate elements together with non-conductive substrates and the insulating layer. The ion gate can be secured by clamping, soldering, screws, pins, but not limited to these examples. The insulating layer can be made from any non-conductive material such as, ceramic, aluminum nitrate, but not limited to these examples.

An alternative embodiment of manufacturing an "Tyndall" type of ion gate for a charged particle stream involves two sets of electrically isolated grid elements, wherein the first set of grid elements is arranged with an offset in respect to the second set of the grid elements, such that the gaps of the first grid element is aligned with the second grid elements; each set of grid elements is applied to alternate potentials when the gate is closed and same potential when the gate is opened. The method involves the steps of: fabricating at least two gate elements by removing portions of a substantially planar metal foil to form a plurality of grid elements; wherein each gate element includes at least one set of grid elements; assembling an insulating layer between the gate elements; and securing the gate elements together.

Figure 8:
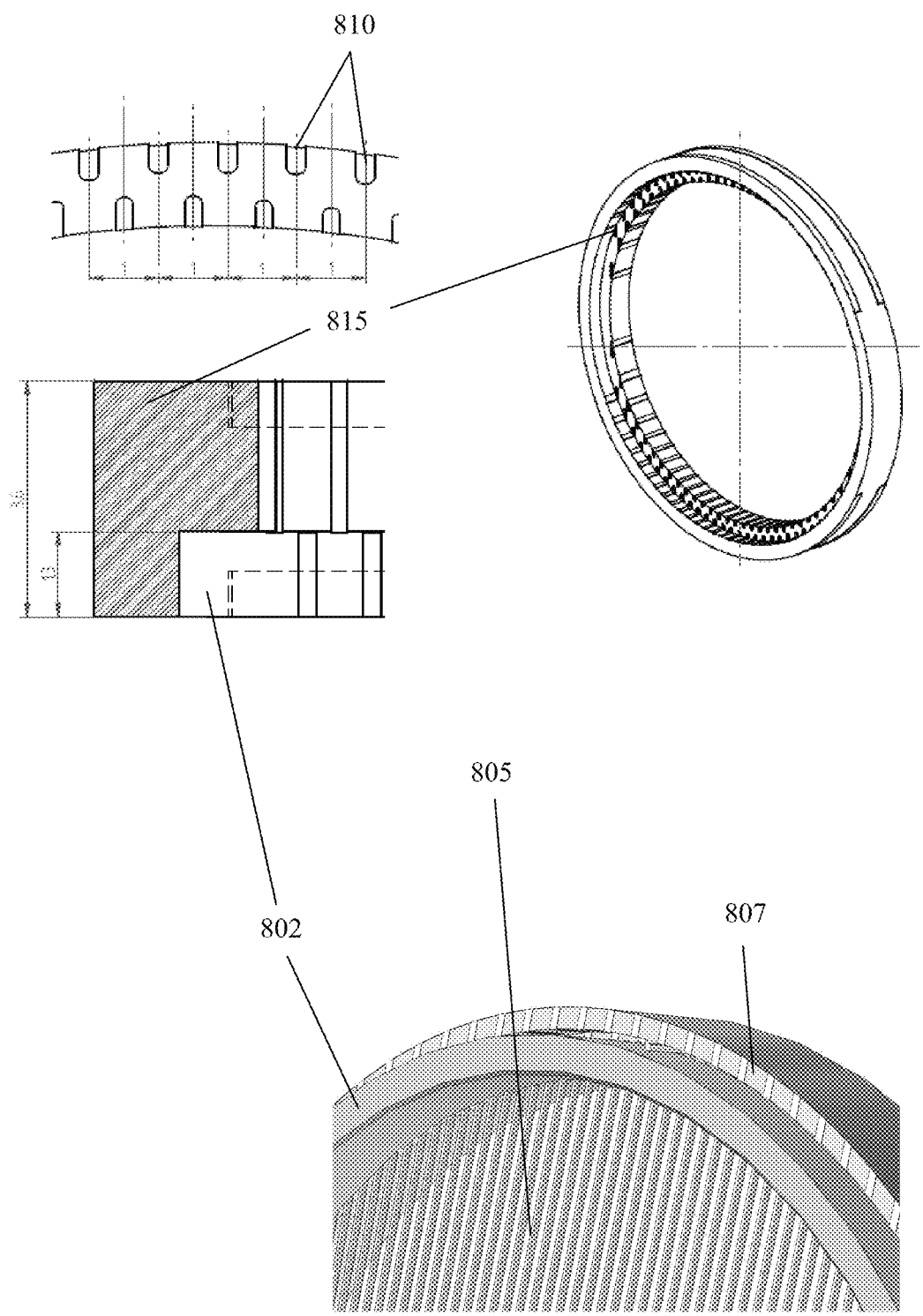
FIG. 8 schematically shows a construction of a Bradbury-Nielsen ion gate using metalized dielectric rings and parallel wires.

In another embodiment of the invention, a metalized dielectric structure is used for the Bradbury-Nielsen gate. A ceramic material is coated with single or multiple layers of metallization materials. The metallization process is commonly finished with a thin layer of nickel, gold or other inert metal for enhanced chemical resistivity. FIG. 8 shows a unique construction method of a Bradbury-Nielsen ion gate using a metalized ceramic material. It is built with a frame ring, a tension ring 802 and parallel wires 805 that are pre-winded on a metal frame. One or the rings, either the frame ring or the tension ring is metalized 815 with a pattern 810 that connects every other wire to each other. In one embodiment, the frame ring has metalized contacts 807 that are 1 mm apart (center to center). During the ion gate construction, the parallel wires are lined up with these contacts and form a firm contact while the tension ring is pushed down into the frame ring. As the wire is selected to match the thermal expansion of the frame ring and tension ring, the wires can be maintained parallel while the IMS is operated under different temperature conditions. The gate control voltage(s) are applied to the wires by attaching an electrical lead to the contact point that is on the outside of the frame ring. Not only for metalized ceramic tube IMS design, the Bradbury-Nielsen ion gate can be used for other analytical instruments.

In various embodiments for symmetric IMS, an ion focusing method can be employed to guide ions to a target collection area on the collector. Suitable focusing methods may include, but are not limited to, static electric field focusing and ion funnel focusing. An ion collector can be segmented to facilitate, collection of ions with specific ion mobility (drift time) or a certain range of mobilities on to different segment of the ion collectors. A segmented Bradbury-Nielsen gate can be used to enhance the separation and collection.

Figure 9:
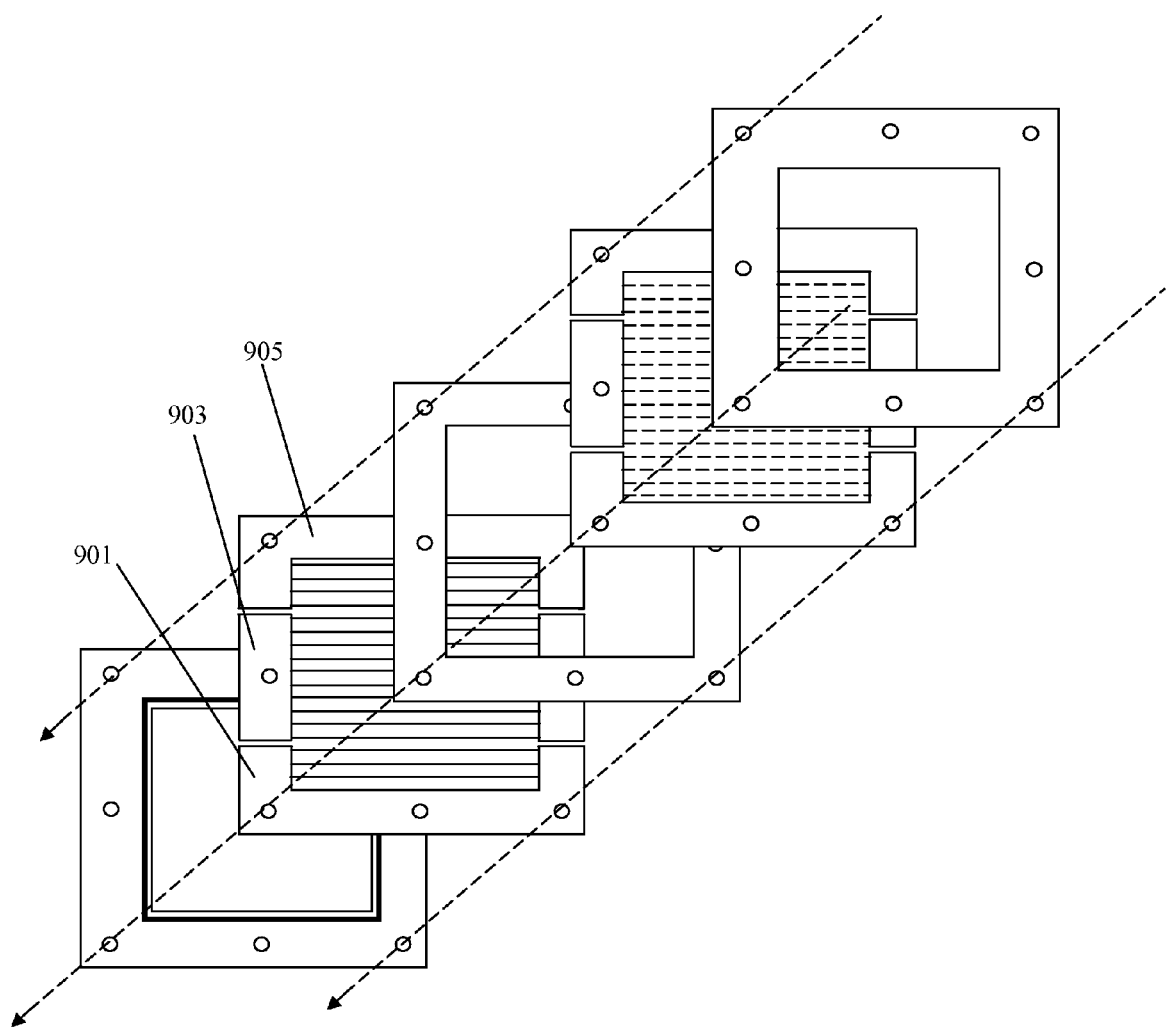
FIG. 9 is a schematic example of a segmented Bradbury-Neilson gate.

In various embodiments of IMS instruments, wherein the Bradbury-Nielsen gate can be segmented. A variety of geometries, including but not limited to parallel, rectangular, concentric ring shape, can be used for the segmentation, referring to FIG. 9, various embodiments can use parallel segmentation. Each segment of the ion gate, for example, 901, 903, and 905, can be controlled to open at a different time. Such a segmented ion gate can be used as either first or second ion gate in a time-of-flight type ion mobility separator. While it is used as the second ion gate in a IMS, multiple portions of ions with different drift time are allow to pass through segmented ion gate, thus collected on different sections of ion collectors, and recovered separately if desired.

In various embodiments, an apparatus of ion gate for an ion mobility separator comprising a segmented Bradbury-Nielson that contains multiple sections of Bradbury-Nielsen gate. The segmented Bradbury-Nielsen gate can be used as a second gate in a time-of-flight type ion mobility separator. The segmented Bradbury-Nielsen gate comprises a variety of geometries which may include but is not limited to: parallel, rectangular, concentric. The ion mobility separator further comprises a segmented ion collector where a plurality of sections of ion collector is inline with the sections of the segmented Bradbury-Nielsen gate.

This invention further describes a method and apparatus of ion gate operation. In one embodiment, an AC voltage is used to close the gate. In a common operation of the Bradbury-Nielsen gate, the ion gate is open when the adjacent grid elements are at the same potential and the ion gate is closed when a DC voltage, e.g. 30V, 50V, 100V, 200V, or −30V, −50V, −100V, −200V are applied on the adjacent grid elements. The voltage creates an electric field that pushes ions toward the grid element that is a lower potential, thus preventing ions from penetrating through the ion gate when closed.

Figure 10:
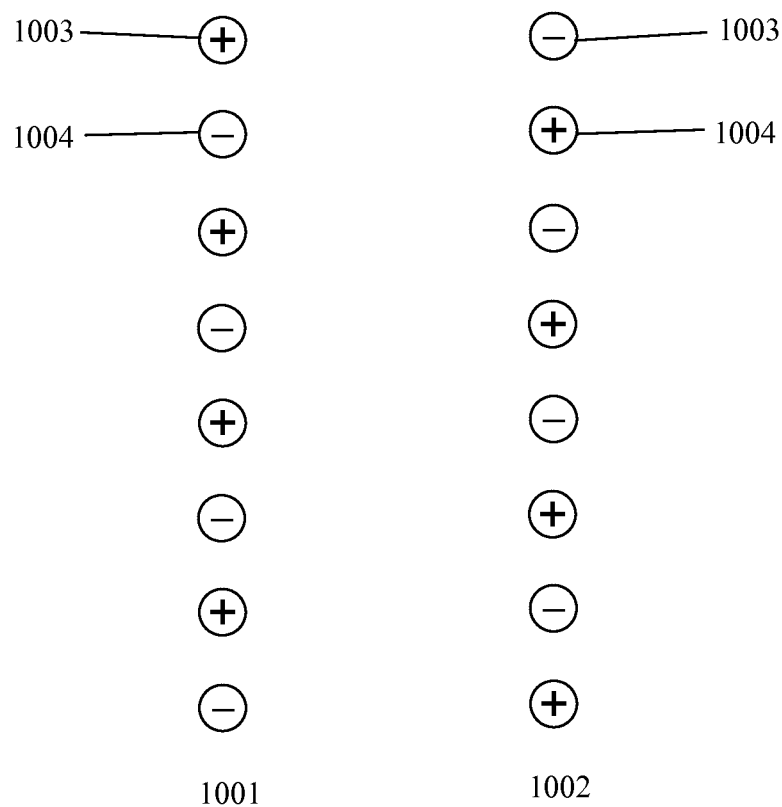
FIG. 10 illustrates an operation method of an ion gate.

During ion mobility measurements, the ion gate is opened for a short period of time, e.g. 100 microseconds, and then closed for a period of time, e.g. 20 millisecond, while ions are traveling in the drift tube. FIG. 10 illustrates a closed ion gate. When the applied voltage is higher than the reference potential, a '+' is shown for the gate wire (i.e. grid element) and when the applied voltage is lower than the reference potential, a '−' is shown for the gate wire. The voltage difference between the adjacent wires causes positive ions to be collected on the (−) wire and negative ions to be collected on the (+) wire. By repeating wire layout pattern of (+) and (−) wires, a large area is covered and ions are prevented to pass through the ion gate. In this embodiment, an AC voltage instead of DC voltage is applied the gate wires. In this case, the potential of each wire is constantly changing. The potential on wire 1003 is '+' and wire 1004 is '−' at the state 1001, and then the potential on wire 1003 is '−' and wire 1004 is '+' at the state 1002. The state 1001 and 1002 repeats at certain frequency. The voltage and frequency of the AC applied to the adjacent wires is optimized to completely close the ion gate. The ion gate is opened by setting all gate wires at the same potential. The new gate configuration and operational method is not limited to be used for ion mobility spectrometer, but can be used for any device that needs to shut off a stream of charged particles.

In a variety of the embodiments, a method for operating an ion gate for a charged particle stream involves opening the ion gate by setting adjacent gate wires (grid elements) at the same potential; closing the ion gate by setting adjacent gate wires at different potentials by applying an AC voltage to the adjacent wires. The AC voltage can be controlled to provide a given frequency and amplitude that that is most suitable for the intended operation. The frequency can be a constant and/or controlled to cover a broad range during a period when the ion gate is closed. Similarly, the amplitude can be a constant and/or controlled in a range during a period of closing the gate. The AC voltage may be a symmetric or asymmetric waveform. In a variety of operation modes, the AC powered ion gate can be operated as such, conducting a series of ion mobility measurements under a series of different frequencies and/or amplitudes, and then integrating the series of ion mobility measurement data into an ion mobility spectrum using common data processing algorithms, such as summing.

Even though many embodiments and examples given in this disclosure refer to ion gate for general IMS device, these devices can be operated under low vacuum, ambient or high pressure conditions. Alternatively, the ion gate can be operated in liquid for liquid phase IMS or other devices, such as electrophoretic devices, where packets of ions need to be formed. The ion gate can also be used under vacuum conditions for generating ion packets for mass spectrometers, such as a time of flight mass spectrometer. This invention discloses gating methods and apparatuses that can be used for any device where packets of charged particles need to be formed.

It is recognized that modifications and variations of the invention disclosed herein will be apparent to those of ordinary skill in the art and it is intended that all such modifications and variations be included with the scope of the appended claims.

What is claimed is:

1. A method for manufacturing an ion gate for a charged particle stream, comprising electrically isolated grid elements that lie in the same plane, the method comprising the steps of:
   a. fabricating at least two gate elements, wherein each gate element includes at least one set of grid elements; and wherein fabricating the gate element includes removing portions of a substantially planar metal foil to form a plurality of grid elements;
   b. assembling an insulating layer between the gate elements;
   c. bending at least one set of grid elements into substantially the same plane of the other set of grid elements with at least one substrate; and
   d. securing the gate elements and the substrates together.

2. The method of claim 1, wherein removing portions of the substantially planar metal foil to form the plurality of grid elements includes etching portions from the foil.

3. The method of claim 2, wherein etching portions from the foil includes etching from one or both sides of the material.

4. The method of claim 1, wherein deflecting the grid elements into the same plane includes interleaving the grid elements.

5. The method of claim 1, wherein fabricating the gate elements includes spacing the grid elements equally.

6. The method of claim 1, wherein fabricating the substrates includes coating a ceramic material with single or multiple layers of metallization materials.

* * * * *